United States Patent
Barnett et al.

(10) Patent No.: US 6,669,947 B2
(45) Date of Patent: Dec. 30, 2003

(54) STRATIFIED AND CRYOGENICALLY STORED VACCINES, PROCESS FOR THEIR PREPARATION

(75) Inventors: Paul Barnett, Pirbright (GB); Vincent Ganne, La Varenne Saint-Hilaire (FR); Jérôme Aucouturier, Chatenay-Malabry (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 6 days.

(21) Appl. No.: 09/972,841

(22) Filed: Oct. 9, 2001

(65) Prior Publication Data

US 2002/0090375 A1 Jul. 11, 2002

(30) Foreign Application Priority Data

Oct. 6, 2000 (FR) .............................. 00 12817

(51) Int. Cl.⁷ .............................. A61K 39/00
(52) U.S. Cl. .............. 424/283.1; 424/184.1; 424/204.1; 424/278.1
(58) Field of Search ............ 424/184.1, 204.1, 424/278.1, 283.1

(56) References Cited

U.S. PATENT DOCUMENTS

| 3,269,905 A | * | 8/1966 | Damaskus ............... 206/459.5 |
| 5,424,067 A | | 6/1995 | Brancq et al. |
| 6,117,432 A | | 9/2000 | Ganne et al. |
| 6,251,407 B1 | | 6/2001 | Ganne |

FOREIGN PATENT DOCUMENTS

| WO | WO 91/00106 | 1/1991 |
| WO | WO 96/32964 | 10/1996 |
| WO | WO 98/17311 | 4/1998 |
| WO | WO 00/03744 | 1/2000 |

OTHER PUBLICATIONS

French–International Search Report dated Jul. 23, 2001, International application No. FA 594203, FR 0012817.

* cited by examiner

*Primary Examiner*—James Housel
*Assistant Examiner*—Myron G. Hill
(74) *Attorney, Agent, or Firm*—Hunton & Williams

(57) ABSTRACT

A composition comprising at least one antigenic medium and at least one adjuvant, wherein the at least one antigenic medium and the at least one adjuvant each comprise one or more phases which are distinct from each other when the composition is in a solid state, and the composition is in the liquid state when its temperature is greater than or equal to 4° C.

4 Claims, No Drawings

STRATIFIED AND CRYOGENICALLY STORED VACCINES, PROCESS FOR THEIR PREPARATION

CROSS REFERENCE TO RELATED APPLICATION

The present application claims the benefit under 35 U.S.C. §119 of French application 00/12817 filed Oct. 6, 2000, the disclosure of which is hereby incorporated by reference.

BACKGROUND OF THE INVENTION (i) Field of the Invention

The present invention relates to a novel vaccine formulation comprising at least one antigen, in particular an antigen of viral, bacterial or parasitic origin, and the method for its preparation.

Currently, the customary vaccines have a storage life which does not exceed 18 to 24 months at +4° C., whether they are oil-based or aqueous. Trials carried out by the Institute for Animal Health (IAH) in Great Britain have shown that oil-based vaccines frozen at −20° C. and at −70° C. lost their activity. Accordingly, commercial vaccines are labeled in this country with the label: "not to be frozen."

Antigens may be stored for longer periods, up to 15 years, at very low temperature, in the form of concentrates. It is essential, in this case, to have means for formulating vaccines close to their storage site in order to avoid loss of time when the vaccine is urgently required.

These considerations have led the applicant to support work aimed at developing vaccines which can be stored for several years, and which are ready to use after thawing.

SUMMARY OF THE INVENTION

According to a first aspect, the subject of the invention is a composition comprising at least one antigenic medium and at least one adjuvant, characterized in that:

(a) the antigenic medium or the antigenic media constitute phases which are distinct from the adjuvant phase or from the adjuvant phases when the composition is in the solid state, and (b) the composition is in the liquid state when its temperature is greater than or equal to 4° C.

The expression distinct phases indicates that, in the composition which is the subject of the present invention, none of the phases is, in the solid state, included, dissolved, emulsified or dispersed in another.

DETAILED DESCRIPTION OF PREFERRED EMBODIMENTS

According to a first particular aspect of the present invention, the various phases constituting the composition in the solid state are adjacent to at most two distinct phases; they are more particularly arranged in a stratified manner in the said composition and are preferably superposed one on top of another.

The expression antigenic medium is understood to mean, in the context of the present invention, a concentrate of antigenic material or a mixture of concentrates of antigenic materials, whether the said concentrates are undiluted or diluted in an appropriate liquid vehicle. The antigenic medium will be called hereinafter "antigenic phase."

The expression antigenic material designates an antigen, a mixture of antigens, a generator in vivo of a compound comprising an amino acid sequence, a mixture of generators in vivo of a compound comprising an amino acid sequence or alternatively a mixture of one or more antigens with one or more generators in vivo of a compound comprising an amino acid sequence.

The expression antigen or at least one generator in vivo of a compound comprising an amino acid sequence designates either killed microorganisms such as viruses, bacteria or parasites, or purified fractions of these microorganisms, or live microorganisms whose pathogenic power has been attenuated.

By way of viruses which may constitute an antigen according to the present invention, there may be mentioned the rabies virus, herpes viruses, such as Aujeszky's disease virus, orthomixoviruses such as influenza virus, picornaviruses such as foot-and-mouth virus or retroviruses such as HIVs.

As microorganism of the bacterial type which may constitute an antigen according to the present invention, there may be mentioned *E. coli* and those of the genera Pasteurella, Furonculosis, Vibrio, Staphylococcus and Streptococcus.

As parasite, there may be mentioned those of the genera Trypanosoma, Plasmodium, and Leishmania.

Recombinant viruses, in particular nonenveloped viruses such as adenoviruses, vaccinia virus, canary poxvirus, herpes viruses or baculoviruses may also be mentioned.

There may also be mentioned a recombinant live nonenveloped viral vector whose genome contains, preferably inserted into a portion which is not essential for the replication of the corresponding enveloped virus, a sequence encoding an antigenic subunit inducing synthesis of antibodies and/or a protective effect against the above mentioned enveloped virus or pathogenic microorganism; such an antigenic subunit is, for example, a protein, a glycoprotein, a peptide or a peptide fraction and/or a fraction which is protective against infection by a live microorganism such as an enveloped virus, a bacterium or a parasite. The exogenous gene inserted into the microorganism is, for example, derived from an Aujeszky virus or an HIV virus.

There may in particular be mentioned a recombinant plasmid consisting of a nucleotide sequence into which an exogenous nucleotide sequence, obtained from a microorganism or from a pathogenic virus, is inserted. The role of the latter nucleotide sequence is to allow the expression of a compound comprising an amino acid sequence, whose role is to trigger an immune reaction in a host organism.

The expression generator "in vivo" of a compound comprising an amino acid sequence designates any biological product capable of expressing the said compound in the host organism into which the said generator in vivo has been introduced. The compound comprising the amino acid sequence may be a protein, a peptide or a glycoprotein. These generators in vivo are generally obtained by methods derived from genetic engineering. More particularly, they may consist of live microorganisms, generally a virus, acting as recombinant vector, into which a nucleotide sequence, in particular an exogenous gene, is inserted. These compounds are known per se and are used in particular as recombinant subunit vaccine. In this regard, reference may be made to the article by M. ELOIT et al., Journal of Virology (1990) 71, 2925–2431 and to the international patent application published under the numbers WO-A-91/00107 and WO-A-94/16681.

The generators in vivo according to the invention may also consist of a recombinant plasmid comprising an exogenous nucleotide sequence, capable of expressing, in a host organism, a compound comprising an amino acid sequence. Such recombinant plasmids and their mode of administration into a host organism were described in 1990 by LIN et al., Circulation 82: 2217, 2221; COX et al., J. of Virol., September 1993, 67, 9, 5664–5667 and in the international application published under the number WO 95/25542. Depending on the nature of the nucleotide sequence contained in the generator in vivo, the compound comprising the amino acid sequence which is expressed in the host organism may:

(i) be an antigen, and may allow an immune reaction to be triggered, (ii) have a curative action on a disease, essentially a disease of a functional nature, which is triggered in the host organism. In this case, the generator in vivo allows treatment of the host, of the gene therapy type. Such a curative action consists, for example, of a synthesis, by the generator in vivo, of cytokines, such as interleukins, in particular interleukin-2. These allow the eliciting or the enhancement of an immune reaction aimed at the selective elimination of cancer cells.

A composition according to the invention comprises an antigen concentration which depends on the nature of this antigen and one the nature of the subject treated. The adequate antigen concentration may be determined in a conventional manner by persons skilled in the art. Generally, this dose is of the order of 0.1 $\mu g/cm^3$ to 1 $g/cm^3$, more generally of between 1 $\mu g/cm^3$ and 100 $mg/cm^3$ of composition in the liquid state.

The concentration of the said generator in vivo in the composition according to the invention depends, here again, in particular on the nature of the said generator and on the host onto which it is administered. This concentration can be easily determined by persons skilled in the art on the basis of a routine experiment. As a guide, it may however be specified that when the generator in vivo is a recombinant microorganism, its concentration in the composition according to the invention may be between $10^2$ and $10^{15}$ microorganisms/$cm^3$ of composition in the liquid state.

When the generator in vivo is a recombinant plasmid, its concentration in the composition according to the invention is generally between 0.01 $g/dm^3$ and 100 $g/dm^3$ of composition in the liquid state.

The form of the antigen concentrates depends essentially on the manner in which the antigens are extracted from the organism or from the molecule containing them and on their nature. The antigen concentrates are not, per se, a subject of the present invention. They may be provided in liquid form, such as the supernatants of antigenic materials or the concentrates of supernatants of antigenic materials or alternatively in solid form, such as lyophilisates.

The composition which is the subject of the present invention may comprise one or more antigens and one or more antigenic phases.

According to a first particular aspect of the present invention, its subject is a composition as defined above, characterized in that the antigenic medium consists of a lyophilisate of antigenic material.

According to a second particular aspect of the present invention, its subject is a composition as defined above, characterized in that the antigenic medium is an aqueous or aqueous-alcoholic phase of antigenic material.

The solvents constituting the antigenic phase are, for example, water, PBS buffer, TRIS buffer or a mixture thereof.

The term adjuvant designates, in the context of the present invention, products which increase reactions of the immune system when they are administered in the presence of antigenic material, whether it is of viral, bacterial, parasitic or synthetic origin. They cause the massive appearance of macrophages at the site of injection, and then in the lymphatic nodules as well as an increase in the production of specific immunoglobulins, antibodies, and they thus stimulate numerous cells involved in the immune defense mechanisms.

The nature of these adjuvants is varied. They may be inorganic salts which are soluble or insoluble in water, aqueous or aqueous-alcoholic solutions of salts, organic compounds, oils or mixtures of these various types of adjuvants. The phase containing one or more adjuvants will be called hereinafter the adjuvant phase.

As customary adjuvants in salt form, there are also metal salts, such as aluminum hydroxide, cerium nitrate, zinc sulfate, colloidal iron hydroxide or calcium chloride. Among these, aluminum hydroxide is most commonly used. These adjuvants are described in the article by Rajesh K. Gupta et al., "Adjuvants, balance between toxicity and adjuvanticity," Vaccine, vol. 11, Issue 3, 1993, pages 993–306.

As examples of water-soluble salts, there are the salts of metal cations and of organic acids possessing at least one phosphoric group or one carboxyl group, such as the salts of glycerophosphoric, acetic, lactic, tartaric, malic, citric, pyruvic, gluconic, glucuronic, fructoheptonic, gluconoheptonic or glucoheptonic, glutamic and aspartic acids or methionine. These salts of metal cations are more particularly chosen from the salts of manganese, aluminum, calcium or zinc, such as for example manganese gluconate, calcium gluconate, zinc gluconate, calcium fructoheptonate, calcium glycerophosphate, soluble aluminum acetate and aluminum salicylate. Some of these adjuvants are described in the international patent applications published under the numbers WO 96/32964 and WO 98/17311.

When water-soluble salts are present in the composition which is the subject of the present invention, their total concentration is between 0.02 $mg/cm^3$ and 3000 $mg/cm^3$, preferably 0.1 $mg/cm^3$ and 1000 $mg/cm^3$ and more particularly from 0.1 $mg/cm^3$ to 150 $mg/cm^3$ of the said composition in the liquid state.

As other adjuvants, there are also surfactants or mixtures of surfactants having an overall HLB number of between 5 and 15. For the purposes of the present invention, the HLB number is calculated by the formula $HLB=20(1-I_s/I_a)$, in which $I_s$ represents the saponification value and $I_a$ the acid value for the said surfactant or for the said mixture of surfactants. These two values, the saponification value and the acid value, are determined by methods described in the European Pharmacopoeia.

As examples of such surfactants, there are modified fatty substances having an overall HLB number of between 6 and 14. The modified fatty substances may be of inorganic, plant or animal origin. As modified fatty substances of inorganic origin, there are modified oils or petroleum origin. As modified fatty substances of plant origin, there are modified vegetable oils, such as modified groundnut, olive, sesame, soybean, wheat germ, grape seed, sunflower, castor, linseed, maize, copra, palm, nut, hazelnut or rapeseed oils. As modified fatty substances of animal origin, there are for example modified spermaceti oil or modified tallow oil.

The expression modified fatty substances designates in general the alkoxylated derivatives of fatty substances and more particularly the alkoxylated derivatives of oils or the alkoxylated derivatives of alkyl esters of oils and more particularly the ethoxylated and/or propoxylated derivatives of oils or the ethoxylated and/or propoxylated derivatives of methyl, ethyl, propyl, linear or branched, or butyl, linear or branched esters of the said oils. The subject of the invention is more specifically a composition as defined above, in which, when the adjuvant is a modified fatty substance or a mixture of modified fatty substances, the latter are chosen from the ethoxylated derivatives of oils having a number of EOs of between 1 and 60 and more particularly from the alkoxylated derivatives of maize oil, mixtures of alkoxylated derivatives of maize oil, having an overall HLB number of between 10 and 14 or from the ethoxylated derivatives of castor oil or mixtures of alkoxylated derivatives of castor oil, having an overall HLB number of between 7 and 10.

When surfactants or mixtures of surfactants having an overall HLB number of between 5 and 15 are present in the composition which is the subject of the present invention, their total concentration is between 0.2 mg/cm$^3$ and 500 mg/cm$^3$, more particularly between 2 mg/cm$^3$ and 500 mg/cm$^3$ of adjuvant and preferably between 50 mg/cm$^3$ and 200 mg/cm$^3$ of the said composition in the liquid state.

As other adjuvants, there are also the alkoxylated derivatives of esters of fatty acids and of polyols or the alkoxylated derivatives of ethers of fatty alcohols and of polyols, and more particularly the triglycerides of alkoxylated fatty acids, the alkoxylated esters of polyglycerol and of fatty acids, the alkoxylated esters of fatty acids with a hexol such as for example sorbitol or mannitol, or the alkoxylated esters of fatty acids with a hexol anhydride such as sorbitan or mannitan.

As fatty acids which are more particularly appropriate for the preparation of these modified esters, there are those comprising from 12 to 22 carbon atoms, advantageously a fatty acid which is liquid at 20° C., such as for example those comprising from 16 to 18 carbon atoms, such as oleic acid, ricinoleic acid or isostearic acid. As examples of these derivatives, there are the ethoxylated derivatives of mannitan oleate having a number of EOs of between 5 and 15, and preferably between 7 and 11.

As other examples of adjuvants, there are the saponins, the lecithins or the compositions comprising:

a) a compound of formula (I):

$$R_1\text{—O—}(G)_x\text{—H} \qquad (I)$$

in which $R_1$ represents a saturated or unsaturated, linear or branched hydrocarbon radical comprising from 1 to 30 carbon atoms, G represents the residue of a saccharide and x represents a decimal number of between 1 and 5 or a mixture of c compounds of formula (I), and if desired b) a compound of formula (II):

$$R_2\text{—OH} \qquad (II)$$

in which $R_2$ represents, independently of $R_1$, a saturated or unsaturated, linear or branched hydrocarbon radical comprising from 8 to 30 carbon atoms or a mixture of compounds of formula (II).

The expression residue of a saccharide designates for G a bivalent radical resulting from the removal, on a sugar molecule, on the one hand, of a hydrogen atom from one of its hydroxyl groups and, on the other hand, of the anomeric hydroxyl group. The term saccharide designates in particular glucose or dextrose, fructose, mannose, galactose, altrose, idose, arabinose, xylose, ribose, gulose, lyxose, maltose, maltotriose, lactose, cellobiose, dextran, talose, allose, raffinose, levoglucan, cellulose or starch. The oligomeric structure $(G)_x$ may exist in any form of isomerism, whether this includes optical isomerism, geometric isomerism or position isomerism; it may also represent a mixture of isomers.

The number x, which represents in the formula (I) the average degree of polymerization of the saccharide, is more particularly between 1 and 3, in particular between 1.05 and 2.5, most particularly between 1.1. and 2.0, and preferably less than or equal to 1.5.

G represents more particularly the glucose residue or the xylose residue.

The radical $R_1$ represents in particular a radical comprising from 5 to 22 carbon atoms chosen from the pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl, docosenyl, heptadecadienyl or decenyl radicals, the said radicals being linear or branched. $R_1$ preferably represents a radical comprising from 8 to 20 carbon atoms, the said radicals being linear or branched.

$R_2$ represents more particularly a radical comprising from 8 to 22 carbon atoms chosen from the octyl, nonyl, decyl, undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl, docosenyl, heptadecadienyl or decenyl radicals, the said radicals being linear or branched.

When the mixture as defined above comprises at least one compound of formula (I) and at least one compound of formula (II), the compound of formula (I)/compound of formula (II) weight ratio is generally between 10/90 and 90/10, more particularly between 10/90 and 60/40.

As other adjuvants, there are oils, and in particular oils known for their low toxicity, whether mineral oils, synthetic oils, vegetable oils or animal oils.

As examples of mineral oils, there are the white mineral oils in conformity with the FDA 21 CFR 172.878 and CFR 178.3620 (a) regulations, such as for example MARCOL™ 52, which is a commercial oil corresponding to the definition of liquid paraffins of the French CODEX or DRAKEOL™ 6VR.

As examples of synthetic oils, there are polyisoprenes, polyisobutenes, hydrogenated polyisobutene, marketed under the name PARLEAM-POLYSYNLANE™ and cited in: Michel and Irene Ash; Thesaurus of Chemical Products, Chemical Publishing Co., Inc. 1986, Volume 1, page 211 (ISBN 0 71313603 0), squalane, marketed under the name PHYTOSQUALAN™ and identified in Chemical Abstracts by the number RN=111-01-3; it is a mixture of hydrocarbons containing more than 80% by weight of 2,6,10,15,19,23-hexamethyltetracosane; there are also squalene, isohexadecane, identified in Chemical Abstracts by the number RN=93685-80-4, which is a mixture of $C_{12}$, $C_{16}$ and $C_{20}$ isoparaffins containing at least 97% of $C_{16}$ isoparaffins, among which the principal constituent is 2,2,4,4,6,8,8-heptamethylnonane (RN=4390-04-9); isododecane.

As other examples of synthetic nonmineral oils, there are the esters of alcohols and fatty acids such as ethyl oleate, isopropyl myristate, oleyl oleate, mono-, di- or triglycerides of fatty acids or the esters of propylene glycol.

As examples of oils of vegetable origin, there are groundnut, olive, sesame, soybean, wheat germ, grape seed, sunflower, castor, linseed, maize, copra, palm, nut, hazelnut or rapeseed oils.

As an example of an oily adjuvant, Freund's adjuvants are very effective; they result from the combination of a mineral oil and of a mannitol ester containing or otherwise a killed mycobacterium.

As examples of oils of animal origin, there is squalane, squalene or spermaceti oil.

When the composition which is the subject of the present invention is in the liquid state, an emulsion, the oil is generally combined with one or more nonionic surfactants which are preferably pharmaceutically acceptable. They should in particular be free of heavy metals and should have very low acid or peroxide values. It is also desirable for them to satisfy the standards for safety tests such as those described by S. S. Berllin, Annals of Allergy, 1962, 20, 473 or the standards for tests of abnormal toxicity described in the European Pharmacopoeia.

As examples of surfactants which may be combined with an oil in the same adjuvant phase, there are those previously described as intrinsically having adjuvant properties. More generally, there are nonionic surfactants of the following chemical families:

The esters or ethers of fatty acids and of a sugar such as sorbitol, mannitol, sucrose or glucose;

The esters of fatty acids and glycerol or a polyol;

The hydrophilic derivatives of these esters obtained by grafting alcohol, ether oxide, carboxyl, amine or amide functional groups, Lecithins, Ethoxylated and/or propoxylated fatty alcohols The fatty chains of these surfactants comprising from 8 to 22 carbon atoms.

Among these surfactants, the ones preferred are those having a fatty chain comprising from 14 to 20 carbon atoms, and more particularly oleic, ricinoleic and ketostearic acids and derivatives thereof and most particularly mannitol oleates and the derivatives of mannitol oleates obtained by grafting hydrophilic functional groups such as for example amide, amine, alcohol, polyol or carboxyl functional groups or ethoxy, propoxy and/or butoxy radicals or mannitan oleates or derivatives thereof; they are obtained by dehydration of the polyhydroxylated carbon chain of mannitol which becomes cyclized at the 1–4 or 2–6 position.

In general, when a nonionic surfactant or a mixture of nonionic surfactants is present in a vaccine composition, combined with an oil in order to express its emulsifying properties, its concentration is between 0.01 mg/ml and 500 mg/ml and preferably between 0.1 mg/ml and 200 mg/ml.

As examples of combination of oils with a nonionic surfactant, there are the products marketed under the name MONTANIDE™, whose characteristics are presented in the following table:

| Name | Composition | Emulsion produced (type; % of aqueous phase by weight) | Conductivity at 25° C. ($\mu S \cdot cm^{-1}$) | Viscosity (mPa.s) |
|---|---|---|---|---|
| MONTANIDE ™ ISA 25 | Mineral oil + mannitol esters | O/W 75% | 5000 | 20 |
| MONTANIDE ™ ISA 25A | Mineral oil + mannitol esters + avridine | O/W 75% | 5000 | 20 |
| MONTANIDE ™ ISA 28 | Mineral oil + mannitol esters + ethyl oleate | O/W 75% | 1000 | 25 |
| MONTANIDE ™ ISA 206 | Mineral oil + mannitol esters + PEG 500* | W/O/W 50% | 1000 | 50 |
| MONTANIDE ™ ISA 50 | Mineral oil + mannitol esters | W/O 50% | 1 | 200 |
| MONTANIDE ™ ISA 708 | Vegetable oil + mannitol esters | W/O 30% | 1 | 70 |

*PEG: polyethylene glycol

According to a third particular aspect of the present invention, the composition which is the subject of the present invention comprises an oily adjuvant phase.

In this case, in the solid state, this oily phase constitutes most particularly the bottom phase of the said composition. Indeed, it has been observed that an emulsion was more easily obtained in this configuration by simple manual stirring at room temperature.

The composition according to the invention may comprise a conventional immune-stimulating agent such as Avridine®, N,N-dioctadecyl-N',N'-bis(2-hydroxyethyl) propanediamine, MDP (muramyl dipeptide) derivatives, in particular threonyl-MDP, mycolic acid derivatives or derivatives of Lipid A.

The phase or phases containing the adjuvant(s) will be called hereinafter adjuvant phase. The composition which is the subject of the present invention may comprise one or more adjuvant phases.

The composition as defined above may comprise, in addition, one or more diluent phases for at least one of the antigenic phases, whose diluent character is expressed in the liquid state, and which, when the composition is in the solid state, are distinct from the antigenic phase or from the antigenic phases and from the adjuvant phase or from the adjuvant phases.

The composition as defined above may comprise, in addition, one or more diluent phases for at least one of the adjuvant phases, whose diluent character is expressed in the liquid state, and which, when the composition is in the solid state, are distinct from the antigenic phase or from the antigenic phases and from the adjuvant phase or from the adjuvant phases.

According to a fourth particular aspect of the present invention, the composition as defined above does not comprises an oily phase.

According to a fifth particular aspect of the present invention, the composition as defined above consists of an antigenic phase and an oily adjuvant phase.

According to a sixth particular aspect of the present invention, the composition as defined above consists of an antigenic phase, an oily adjuvant phase and a diluent phase for the antigenic phase.

In the latter two configurations, in the composition as defined above, in the solid state, the oily phase preferably constitutes the bottom layer and the antigenic phase the top phase.

According to a second aspect of the present invention, its subject is a method for preparing a composition as defined above, characterized in that:

a) a first of the adjuvant, diluent or antigenic phases, which is liquid at room temperature, is brought to a temperature of less than or equal to its solidification point so as to form a first solid phase, b) a second of the other antigenic, adjuvant or diluent phases is added, in the liquid state, over the solid phase prepared in a), and then the new combination is brought to a temperature of less than or equal to the lowest solidification point of the two phases so as to form a solid combination with two distinct phases, c) where appropriate, a new antigenic, adjuvant or diluent phase is added, in the liquid state, over the said solid combination prepared in step b), and then the new combination is brought to a temperature of less than or equal to the lowest solidification point of the three phases so as to form a solid combination with three distinct phases, and d) the sequence of operations carried out in step c) is, where appropriate, repeated until the last of the antigenic, adjuvant or diluent phases constituting the said composition has been frozen.

More specifically, to prepare a composition consisting of an antigenic phase, an oily adjuvant phase and optionally a diluent phase for the antigenic phase, in the method as defined above, the phase used in step a) is the oily adjuvant phase, the phase used in step b) is either the diluent phase, when the composition comprises one, or the antigenic phase, and the phase used, where appropriate, in step c) is the antigenic phase.

Still more specifically, to prepare a vaccine emulsion of an antigenic phase and an oily phase consisting of a combination of one or more oils with one or more non ionic surfactants, the process comprises the following main steps:

(a) Required volumes of the oily phase are aliquoted into a desired primary container, placed in the ultra-low temperature gaseous phase of liquid nitrogen, and snap frozen;

(b) The frozen phase obtained from step 1, is momentarily removed from the low temperature environment and the prerequisite volume of aqueous buffer is carefully layered onto the top of the frozen phase to form two distinguishable layers or stratifications; this is immediately returned to the ultra-low temperature environment to snap freeze the aqueous buffer;

(c) The stratified combination obtained from step (b), is momentarily removed from the low temperature environment and the prerequisite volume of concentrated antigen is then carefully layered onto the top of the frozen buffer layer of said stratified combination to form a third distinguishable layer or stratification; this is immediately returned to the ultra-low temperature environment to snap freeze the antigen concentrate.

According to a third aspect of the present invention, its subject is the composition as defined above, for carrying out a method of treating the human or animal body by subcutaneous injection, by intramuscular injection or by intravenous injection.

More specifically, when required, the stratified and cryogenically stored (SACS) vaccine is thawed at room temperature, mixed by simply agitation and administered into the target host.

The composition according to the invention may be used as a preventive or curative medicament. Depending on the nature of the antigen or the generator in vivo, a composition according to the invention may be administered to fish, crustacea such as shrimp, poultry, in particular geese, turkeys, pigeons and chickens, to Canidae such as dogs, to Felidae such as cats, to pigs, to primates, to Bovidae, to Ovidae and to horses.

According to a last aspect of the present invention, its subject is a method for the freezing preservation of a composition comprising at least one antigenic medium, at least one adjuvant and optionally at least one diluent for the said antigenic medium and/or for the said adjuvant, characterized in that:

a) a first of the adjuvant, diluent or antigenic phases, which is liquid at room temperature, is brought to a temperature of less than or equal to its solidification point so as to form a first solid phase, b) a second of the other antigenic, adjuvant, or diluent phases is added, in the liquid state, over the solid phase prepared in a), and then the new combination is brought to a temperature of less than or equal to the lowest solidification point of the two phases so as to form a solid combination with two distinct phases, c) where appropriate, a new antigenic, adjuvant or diluent phase is added, in the liquid state, over the said solid combination prepared in step b), and then the new combination is brought to a temperature of less than or equal to the lowest solidification point of the three phases so as to form a solid combination with three distinct phases, d) the sequence of operations carried out in step c) is, where appropriate, repeated until the last of the antigenic, adjuvant or diluent phases constituting the said composition has been frozen, and e) the composition thus frozen is kept at a temperature lower than the lowest freezing point of the said phases constituting it.

Unexpectedly, it was observed that while the vaccines in the form of water-in-oil (W/O), oil-in-water (O/W) and water-in-oil-in-water (W/O/W) emulsions lost their activity after being stored at −20°C. for 7 months, those stored according to the method as defined above, under the same conditions of temperature and duration, remained just as active.

More particularly, to preserve a composition consisting of an antigenic phase, an oily adjuvant phase and optionally a diluent phase for the antigenic phase, in the method as defined above, the phase used in step a) is the oily adjuvant phase, the phase used in step b) is either the diluent phase, when the composition comprises one, or the antigenic phase, and the phase used, where appropriate, in step c) is the antigenic phase.

The following examples illustrate the invention without however limiting it.

1. First Sequence Of Experiments

A. Preparation of Compositions According to the Invention 5 milliliter (ml) doses of vaccine for the treatment of foot-and-mouth disease are prepared in the following manner:

1—2.5 ml samples of MONTANIDE™ ISA206, consisting of the combination of about 2.15 ml of injectable mineral oil with 0.35 ml of a mixture of mannitan oleate and PEG 500, are frozen at about −18° C.;

2—After freezing, the samples are removed from the freezer and immediately supplemented with 2.45 ml of phosphate buffer (PBS) and then refrozen;

3—Once again, the samples are removed from the freezer and immediately supplemented with 0.05 ml of concentrate containing 10 mg/ml of foot-and-mouth disease antigen and refrozen so as to form the vaccine compositions $A_i$.

B. Preparation of Compositions of the State of the Art 5 ml doses of vaccines for the treatment of foot-and-mouth disease in ovines are prepared by mixing 2.5 ml of an oily adjuvant, MONTANIDE™ ISA206, consisting of the combination of about 2.25 ml of injectable mineral oil with 0.25 ml of a mixture of mannitan oleate, which is emulsified according to the method described in international publication WO 91/00106, in 2.5 ml of a PBS solution containing 0.5 mg of foot-and-mouth antigen so as to form vaccine compositions in the form of water-oil-water emulsions (compositions $B_j$).

C. Comparative Study of Vaccine Efficacy

The efficacy of the vaccines according to the invention is studied by comparing them with the efficacy of placebo doses of 5 ml containing 2.5 ml of MONTANIDE™ ISA206 and 2.5 ml of PBS buffer (compositions $P_k$) and with those of the state of the art.

Trial 1

1 ml of various concentrations of antigens is injected into groups of 5 guinea pigs using compositions $A_i$, which are used immediately after thawing, optional dilution in PBS and manual stirring so as to form an emulsion just before injection. The same procedure is carried out with placebo compositions.

The vaccine activity is determined after a booster injection at 28 days by ELISA assay of the IG1 in order to determine the humoral immune response and of the IG2 a in order to determine the cellular immune response.

Fore each group of five guinea pigs, the number of animals protected 90 days after the first vaccination are counted.

The results, expressed as % of animals protected, are presented in the following table:

| Compositions | Duration of frozen storage after preparation (in months) | Dilution of the composition | | |
|---|---|---|---|---|
| | | none | ⅓ | 1/9 |
| $A_1$ | 0 | 100% | 100% | 100% |
| $A_2$ | 5 months | 100% | 100% | 80% |
| $A_3$ | 7 months | 100% | 100% | 100% |
| $P_1$ | 0 | 0% | | |
| $P_2$ | 5 months | 0% | | |
| $P_3$ | 7 months | 0% | | |

Trial 2

1 ml of various concentrations of antigens are injected into groups of 5 guinea pigs using compositions $A_4$, stored for 7 months at −20° C., used immediately after thawing, optional dilution in PBS and manual stirring so as to form an emulsion just before injection. The same procedure is carried out with placebo compositions $P_4$ and a W/O/W emulsion (composition $B_4$), stored for 7 months at −20° C. The vaccine activity is determined after a booster injection at 28 days, by ELISA assay of the IG1, in order to determine the humoral immune response and of the IG2a in order to determine the cellular immune response. For each group of five guinea pigs, the number of animals protected 90 days after the first vaccination are counted and the $PD_{50}$ index, which expresses the degree of dilution below which less than 50% of the group is protected, is determined. The results, expressed as % of animals protected, are presented in the table below:

| Compositions | Dilution of the compositions | | | | |
|---|---|---|---|---|---|
| | none | ⅓ | 1/9 | 1/27 | 1/81 |
| $A_4$ | 100% | 100% | 100% | 100% | 75% |
| $B_4$ | 100% | 100% | 100% | 75% | 25% |
| $P_4$ | 0% | | | | |

A $PD_{50}$ index equal to 106.5, which corresponds to a dilution of the composition of about 1/100 is deduced by extrapolation for the compositions $A_4$, and a $PD_{50}$ index equal to 46.71, which corresponds to a dilution of the composition of about 1/50, is deduced by extrapolation for the compositions $B_4$.

This trial showed that a vaccine composition, comprising, in the solid state, an antigenic phase and an adjuvant phase which are distinct in relation to each other, the term distinct being understood in the definition given in the present description, when used after a 7-month storage at 20° C., is more effective than a vaccine composition containing the same constituents but which was stored for the same period and at the same temperature in the form of an emulsion (froze) of the various phases.

Trial 3

1 ml of various concentrations of antigens are injected into groups of 5 guinea pigs using vaccine compositions according to the invention, stored for 7 months at −20° C., thawed, stored at +40° C. (in the liquid state) for 4 months (compositions $A_5$) or 7 months (composition $A_6$) and used in various optional [lacuna] in PBS. The same procedure is carried out with placebo compositions $P_5$ and $P_6$. The vaccine activity is determined after a booster injection at 28 days, by ELISA assay of the IG1s in order to determine the humoral immune response and of the IG2a in order to determine the cellular immune response. For each group of five guinea pigs, the number of animals protected 90 days after the first vaccination are counted. The results, expressed as % of animals protected, are presented in the following table:

| Compositions | Duration of storage at +4° C., after thawing in months | Dilution of the compositions | | |
|---|---|---|---|---|
| | | none | ⅓ | 1/9 |
| $A_5$ | 4 months | 100% | 100% | 100% |
| $A_6$ | 7 months | 100% | 100% | 100% |
| $P_5$ | 4 months | 0% | | |
| $P_6$ | 7 months | 0% | | |

This trial showed that the freezing time has no harmful effect on subsequent storage of the vaccine composition in the liquid state. In the event of urgent interventions, the frozen compositions according to the invention can therefore be transported to their site of use, under refrigeration conditions identical to those of the state of the art (+4° C.).

2. Second Sequence of Experiments

A. Vaccine Preparation

Vaccine formulations, incorporating FMDV $O^1$ Lausanne inactivated antigen as either water-in-oil-in-water (W/O/W) emulsion with Montanide™ ISA 206, or as a oil-in-water (O/W) emulsion with Montanide™ ISA 25, were prepared conventionally (Barnett et al., Vaccine 14 (13), pages 1187–1198; 1996), or by the novel procedure, using antigen concentrate held by the International Vaccine Bank (IVB) over liquid nitrogen with a $PD_{50}$ value of 41 per bovine dose.

The formulated vaccine contained 5.62 μg of 146S antigen per 2 ml bovine dose.

The novel formulation procedure involved 4 main steps as follows:

1. Oil adjuvants Montanide ISA 206 or 25, at the required volume, were aliquoted into the desired primary container, placed in the ultra-low temperature gaseous phase of liquid nitrogen, and snap frozen.
2. The frozen oil adjuvant is then momentarily removed from the low temperature environment and the prerequisite volume of aqueous buffer is carefully layered onto the top of the frozen oil adjuvant to form two distinguishable layers or stratifications. This is immediately and carefully returned to the ultra-low temperature gaseous phase of liquid nitrogen to snap freeze the aqueous buffer.
3. The frozen oil adjuvant and aqueous buffer layers are again momentarily removed from the low temperature environment and the prerequisite volume of concentrated antigen is then layered on top of the frozen buffer. This is immediately returned to the ultra-low temperature environment to snap freeze the antigen concentrate.
4. When required, the stratified and cryogenically stored (SACS) vaccine are thawed at room temperature, mixed by simply agitation and administered into the target host.

For comparison purposes conventionally formulated vaccines, adjuvanted with Montanide ISA 206 and 25, were also snap frozen by placing in the ultra-low temperature gaseous phase of liquid nitrogen.

B. In Vivo Potency Tests

Vaccine preparations were tested in female Duncan-Hartley guinea pigs, approximately 400–500 gm in weight. Each group of five animals received a specific volume of vaccine of either 1 ml, 0.33 ml or 0.11 ml, administered subcutaneously. Animals were challenged 28 days post-vaccination with $3 \times 10^3$ $ID_{50}$ of the homologous guinea pig adapted virus, injected by the intraplantar route. All animals were monitored closely for 7–10 days, and immunized guinea pigs were considered protected if the virus failed to generalized beyond the challenge site.

Later experiments incorporated dilutions of vaccine instead of the reduced volume dose described previously. Essentially vaccines were diluted in a similarly formulated vaccine that did not contain the antigen component so that the antigen but not the adjuvant was diluted. The dilution range used was three-fold from neat to 1/81. Again animals were challenged 28 days post-vaccination with $3 \times 10^3$ $ID_{50}$ of the homologous guinea pig adapted virus, injected by the intraplantar route and monitored as described previously. This dilution range allowed the potency ($PD_{50}$) of the vaccine to be calculated by the method of Karber (Karber., Arch. Exp. Pathol. Pharmakol. 1931, 162, 480).

Results

In the first trial, SACS vaccines based on either Montanide™ ISA 206 or Montanide™ ISA 25 were examined for their stability at ultra-low temperature over a 7 months period. Using a divided dose regime results were encouraging showing that in the absence of any loss in vaccine potency the procedure was not detrimental to either adjuvanted formulation (Table 1).

TABLE 1

Potency of SACs vaccines based on Mantanide ™ ISA 25 (oil-in-water) and Montanide ™ ISA 206 (water-in-oil-in-water) adjuvanted vaccines following storage at +4° C. for up to 7 months

| Vaccine | 0 day | | | 5 months | | | 7 months | | |
|---|---|---|---|---|---|---|---|---|---|
| | 1.0 ml | 0.33 ml | 0.11 ml | 1.0 ml | 0.33 ml | 0.11 ml | 1.0 ml | 0.33 ml | 0.11 ml |
| SACS ISA 206 | 100 | 100 | 100 | 100 | 100 | 90 | 100 | 100 | 100 |
| SACS ISA 25 | 100 | 100 | 100 | 100 | 100 | 100 | 100 | 100 | 100 |

*Figures show the percentage of guinea pigs protected per dosage group.

In the second trial, SACS vaccine's based on Montanide ISA 206 or ISA 25 were diluted in similarly treated vaccine without the antigen component and compared to the $PD_{50}$ value of conventionally formulated vaccines (Table 2).

TABLE 2

Potency (PD50) estimation of SACS ISA 206 and ISA 25 vaccines

| Vaccine | Dilutions | | | | | Control | $PD_{50}$ value |
|---|---|---|---|---|---|---|---|
| | 1/1 | 1/3 | 1/9 | 1/27 | 1/81 | | |
| SACS ISA 206 | 100 | 100 | 100 | 100 | 75 | 0 | 106.5** |
| SACS ISA 25 | 100 | 100 | 100 | 60 | 60 | 0 | 58.2 |

*Figures show the percentage of guinea pigs protected per dosage group.
**This compares with conventionally made oil vaccine using the same batch of Montanide ISA 206 with a $PD_{50}$ value of 46.71, which was performed on a separate occasion.

Further studies showed that samples of SACS vaccines using the two mineral oil adjuvants when thawed mixed and subsequently stored at +4° C. still remained potent after 7 months (Table 3). This compared well to previous observations on conventionally formulated emergency vaccines composed of the same adjuvants (Barnett et al., Vaccine 14 (13), pages 1187–1198; 1996).

TABLE 3

Potency of SACs vaccines based on Montanide ISA 25 (oil-in-water)
and 206 (water-in-oil-in-water) adjuvanted vaccines following thawing,
mixing and storage at +4° C. for up to 7 months

| Vaccine | 0 day | | | 4 months | | | 7 months | | |
|---|---|---|---|---|---|---|---|---|---|
| | 1.0 ml | 0.33 ml | 0.11 ml | 1.0 ml | 0.33 ml | 0.11 ml | 1.0 ml | 0.33 ml | 0.11 ml |
| SACS ISA 206 | 100 | 100 | 100 | 100 | 100 | 100 | 100 | 100 | 100 |
| SACS ISA 25 | 100 | 100 | 100 | 100 | 100 | 100 | 100 | 100 | 100 |

*Figures show the percentage of guinea pigs protected per dosage group.

Interestingly, snap freezing conventionally formulated oil emulsion generated differing results and was dependent on the oil adjuvant used. Whilst conventional vaccine formulated with ISA 25 showed a considerable loss in potency (Table 4) the Montanide™ ISA 206 based vaccine did not seem to be affected by snap freezing in the gaseous phase of liquid nitrogen. This was contrary to what had been observed previously when storing this type of vaccine at −20° C. and −70° C. and suggests that the novel procedure of formulating by stratification has greater benefits to some "ready-to-formulate" oil adjuvants than others.

TABLE 4

Potency of conventionally formulated
vaccines based on Montanide ™ ISA 25 (oil-in-water)
and Montanide ™ ISA 206 (water-in-oil-in-water)
adjuvants following snap freezing and subsequent thawing

| | 0 day | | |
|---|---|---|---|
| Vaccine | 1.0 ml | 0.33 ml | 0.11 ml |
| ISA 206 | 100 | 100 | 100 |
| ISA 25 | 75 | 25 | 0 |

*Figures show the percentage of guinea pigs protected per dosage group.
**Conventionally formulated vaccine which was snap frozen in the gaseous phase of liquid nitrogen and thawed immediately afterwards before administration.

To examine this further the potency of a conventionally formulated ISA 206 vaccine that had been snap frozen was compared with the same batch not snap frozen but left at +4° C. overnight (Table 5). These results suggest that for vaccine formulated with Montanide ISA 206 the vaccine can be stored frozen providing the freezing procedure is rapid and at very low temperature.

TABLE 5

Potency (PD$_{50}$) estimation of conventionally formulated Montanide
ISA 206 adjuvanted with and without snap freezing

| Vaccine | Dilutions | | | | | Control | PD$_{50}$ value |
|---|---|---|---|---|---|---|---|
| | 1/1 | 1/3 | 1/9 | 1/27 | 1/81 | | |
| Snap frozen ISA 206 | 100 | 100 | 100 | 90 | 100 | 0 | 83.58 |
| Unfrozen ISA 206 | 100 | 100 | 100 | 100 | 90 | 0 | 83.58 |

*Figures show the percentage of guinea pigs protected per dosage group.

What is claimed is:

1. A method for preparing a composition comprising at least one antigenic phase, at least one adjuvant phase, and optionally a diluent phase, wherein the at least one antigenic phase and the at least one adjuvant each comprise one or more phases which are distinct from each other when the composition is in a solid state, and the composition is in the liquid state when its temperature is greater than or equal to 4° C., said method comprising the steps of:
   a) bringing a first of an adjuvant, diluent or antigenic phase, which is liquid at room temperature, to a temperature of less than or equal to its solidification point so as to form a first solid phase,
   b) adding a second antigenic, adjuvant or diluent phase, in the liquid state, over the solid phase prepared in a), and then bringing the new combination to a temperature of less than or equal to the lowest solidification point of the two phases so as to form a solid combination with two distinct phases,
   c) adding, where appropriate, a new antigenic, adjuvant or diluent phase, in the liquid state, over said solid combination prepared in step b), and then bringing the new combination to a temperature of less than or equal to the lowest solidification point of the three phases so as to form a solid combination with three distinct phases, and
   d) repeating the sequence of operations carried out in step c), where appropriate, until the last of the antigenic, adjuvant or diluent phases comprising said composition has been frozen wherein the frozen composition comprises at least one antigenic phase, at least one adjuvant phase, and optionally at least one diluent phase.

2. The method as defined in claim 1, for preparing a composition comprising an antigenic phase, an oily adjuvant phase and optionally a diluent phase for the antigenic phase, in which the phase used in step a) is the oily adjuvant phase, the phase used in step b) is either the diluent phase, when the composition comprises one, or the antigenic phase, and the phase used, where appropriate, in step c) is the antigenic phase.

3. Method for freezing preservation of a composition comprising at least one antigenic phase, at least one adjuvant phase and optionally at least one diluent phase for said antigenic phase and/or for said adjuvant, comprising the steps of:
   a) bringing a first of the adjuvant, diluent or antigenic phase, which is liquid at room temperature, to a temperature of less than or equal to its solidification point so as to form a first solid phase,
   b) adding a second antigenic, adjuvant or diluent phase, in the liquid state, over the solid phase prepared in a), and then bringing the new combination to a temperature of less than or equal to the lowest solidification point of the two phases so as to form a solid combination with two distinct phases, c) adding, where appropriate, a new antigenic, adjuvant or diluent phase, in the liquid state, over said solid combination prepared in step b), and then bringing the new combination to a temperature of less than or equal to the lowest solidification point of the three phases so as to form a solid combination with three distinct phases, d) repeating the sequence of operations carried out in step c), where appropriate, until the last of the antigenic, adjuvant or diluent phases constituting the said composition has been frozen, and e) keeping the composition thus frozen at a temperature lower than the lowest freezing point of said phases constituting it wherein the frozen composition comprises at least one antigenic phase, at least one adjuvant phase, and optionally at least one diluent phase.

4. The method as defined in claim 3, for preserving a composition comprising an antigenic phase, an oily adjuvant phase and optionally a diluent phase for the antigenic phase, in which the phase used in step a) is the oily adjuvant phase, the phase used in step b) is either the diluent phase, when the composition comprises one, or the antigenic phase, and the phase used, where appropriate, in step c) is the antigenic phase.

* * * * *

UNITED STATES PATENT AND TRADEMARK OFFICE
Certificate

Patent No. 6,669,947 B2                                        Patented: December 30, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul Barnett, Pirbright, Great Britain.

Signed and Sealed this Thirtieth Day of May 2006.

*JAMES HOUSEL*
*Supervisory Patent Examiner*
*Art Unit 1648*